Figure 1:
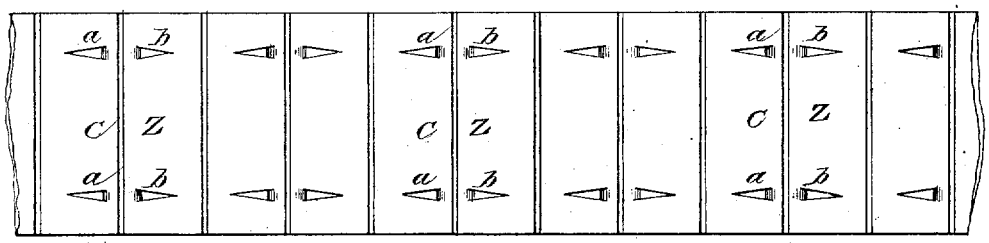

4 Sheets—Sheet 1.

I. L. PULVERMACHER.

ELECTRO-GALVANIC CHAINS, BANDS, &c.

No. 7,210. Reissued July 4, 1876.

Witnesses:
Donn F. Tortchell
Will H. Dodge

Inventor:
I. L. Pulvermacher
by Dodgerson
Attys.

THE NORRIS PETERS CO., PHOTO-LITHO., WASHINGTON, D. C.

I. L. PULVERMACHER.

ELECTRO-GALVANIC CHAINS, BANDS, &c.

No. 7,210. Reissued July 4, 1876.

Witnesses:
Donn F. Tortchell
Will H. Dodge

Inventor:
I. L. Pulvermacher
by Dodge & Son
Attys.

THE NORRIS PETERS CO., PHOTO-LITHO., WASHINGTON, D. C.

I. L. PULVERMACHER.
ELECTRO-GALVANIC CHAINS, BANDS, &c.
No. 7,210. Reissued July 4, 1876.
Fig. 16.
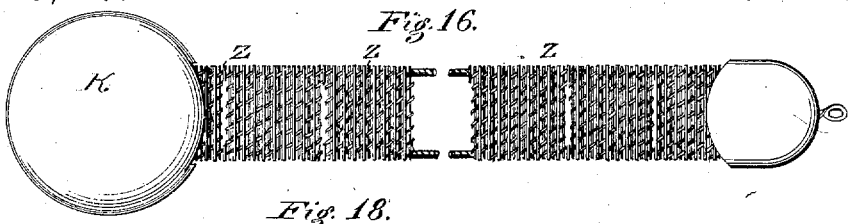
Fig. 18.
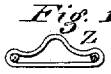
Fig. 17.
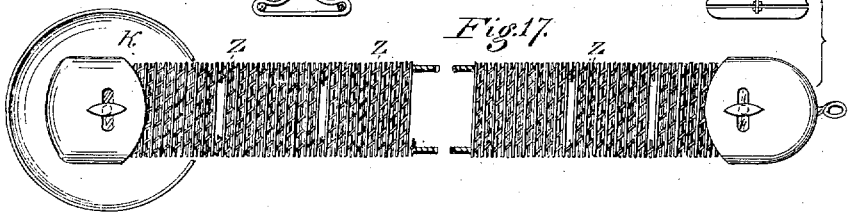
Fig. 37.
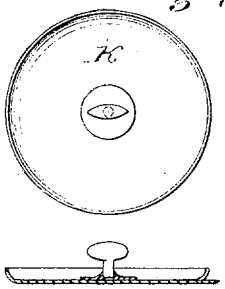
Fig. 38.
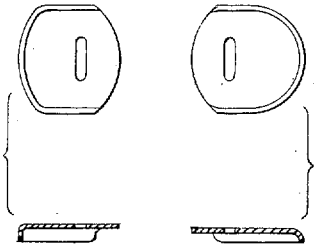
Fig. 39.
Fig. 40.
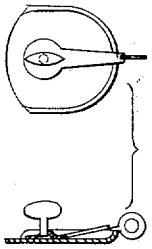
Fig. 27.
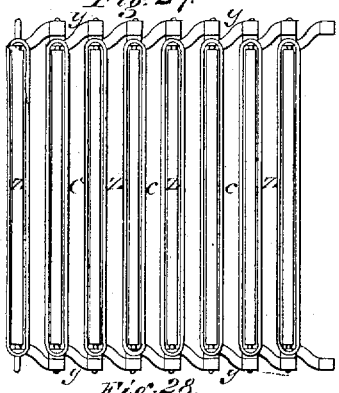
Fig. 28.
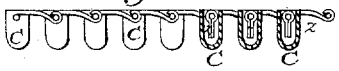
Fig. 24.
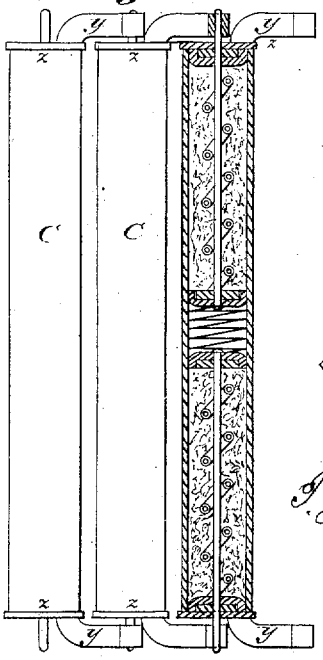
Fig. 23.
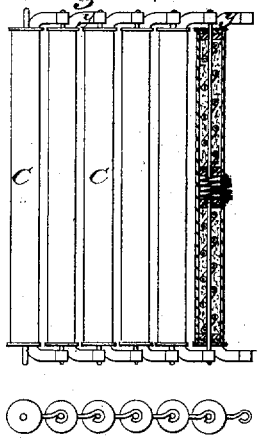
Witnesses:
Donald Tutchell
Will W. Dodge.
Inventor:
I. L. Pulvermacher,
by Dodgerson
Attys.
THE NORRIS PETERS CO., PHOTO-LITHO., WASHINGTON, D. C.

I. L. PULVERMACHER.

ELECTRO-GALVANIC CHAINS, BANDS, &c.

No. 7,210. Reissued July 4, 1876.

Witnesses:
Dwan A. Tuttehell
Will H. Dodge

Inventor:
I. L. Pulvermacher
by Dodgerson
Attys.

THE NORRIS PETERS CO., PHOTO-LITHO., WASHINGTON, D. C.

UNITED STATES PATENT OFFICE.

ISAAC LOUIS PULVERMACHER, LONDON, ENGLAND, ASSIGNOR TO JOHN E. HETHERINGTON, OF CINCINNATI, OHIO.

IMPROVEMENT IN ELECTRO-GALVANIC CHAINS, BANDS, &c.

Specification forming part of Letters Patent No. 120,772, dated November 7, 1871; reissue No. 7,210, dated July 4, 1876; application filed April 28, 1876.

DIVISION D.

*To all whom it may concern:*

Be it known that I, ISAAC LOUIS PULVERMACHER, of London, England, have invented certain new and useful Improvements in Electro-Galvanic Chains, Bands, &c.; and I do hereby declare that the following is a full, clear, and exact description thereof, reference being had to the accompanying drawings, making part of this specification, and to the letters of reference marked thereon, like letters indicating like parts wherever they occur.

To enable others skilled in the art to construct and use my invention, I will proceed to describe it.

The object of the first part of my present invention is to manufacture chains, bands, articles of dress, or wearing apparel, with metal plates or pieces of metal so arranged that they can be used with a self sustaining and permanent electrical or galvanic action, derived either from an exciting liquid or by the perspiration thrown off from the body of the wearer; and this I accomplish by sewing, looping, or otherwise securing the plates or pieces of metal upon a backing of porous or absorbent material, such material having a sticky substance, such as wax, diachylon, or sparadrap, on the exposed parts, to enable the patient to fasten the article upon his body at the part affected; or, in lieu of the backing being covered with the sticky substance, the plates or the pieces of metal themselves may be coated over a portion of their surfaces with such substance. The plates or pieces of metal may be of any shape, perforated or not; or they may have pins or projections in or on them; or they may be formed of strips wound into flat spirals or helices, or of beads, eyelets, or tinsels. If spirals are used, they may be wound upon a core, or secured to a backing after they are wound. In that case an independent core or lining, elastic or not, could be introduced into them, the filling-in materials being of a porous or absorbent nature; or it may be a chemical salt of exciting or electro-depolarizing action; or the spirals may be left open and the exciting liquid applied to the backing in any convenient manner. The backing may also be formed of threads wound upon portions of the spirals to prevent false contacts, and these threads may form the means of combining the elements in voltaic arrangement without interfering with the flexibility and elasticity of the spirals. Beads or other pieces may be joined in sections by looping the opposite metals of the elements together; or the core or lining may be composed of a combination of elastic and non-elastic material, one of them forming the absorbent, and the other the flexible and elastic, portion of the article. In some cases the plates or pieces of metal forming the elements are to be soldered together, either before or after they are stamped out or otherwise prepared. If this is done before stamping, I propose to solder the overlapping edges of long strips together to prevent waste of labor and material. In other cases the pins of one metal could be soldered to the pins of the other metal after they had been passed through the backing or the lining and bent down to touch, to fasten and establish regular voltaic contacts.

I have in the accompanying drawing shown several shapes of plates, strips, or pieces of metal, which are cut by dies, in a press or otherwise; but I do not restrict myself to those shapes, as the pieces may be cut to any pattern found desirable.

Figure 2:
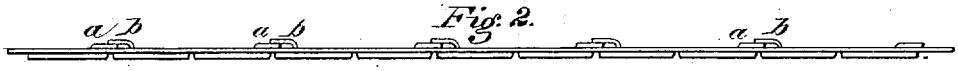

Figure 1 is a view of a part of a band or belt with flat rectangular plates, C Z, which can be secured upon or to a backing of waterproof or other material by the tongues or lips *a b*, in the manner represented in Fig. 2—that is, by bending the tongues outward, and then passing their points through the meshes of the fabric forming the backing, and afterward pressing them down upon the other side. The tongues are of such a length that when those of one plate (say the copper) are bent over toward those of the other plate, (say zinc,) they are brought into contact to complete the voltaic connection and to form a battery. These tongues, when in contact, are then soldered together to secure permanent contact, and also to prevent their becoming disconnected.

In all the figures where copper and zinc, or other metals with corresponding properties, are referred to, they are, for the sake of clearness, indicated with C and Z.

Figure 3:
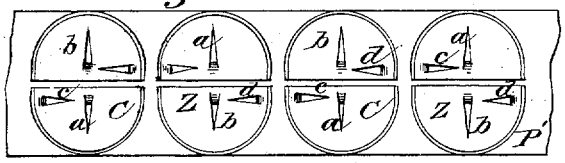

Fig. 3 represents a series of plates, C Z, of a different shape, which are formed with tongues or lips in a similar manner to those above referred to, so that they can be fastened into the fabric. These plates are arranged in voltaic order, so that the current can flow in a zigzag manner, the two poles being represented by P P′.

By folding these plates one above another and placing a wet conductor between them, the band can be used also as a pole-battery. There are additional tongues *c d* formed in these plates for directing the current into the proper direction, the tongues being bent over and fastened in a similar manner to those marked *a b*.

Figure 4:
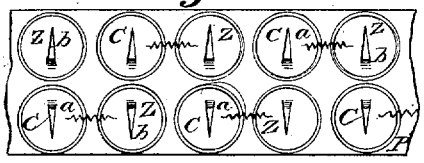

Fig. 4 is a view of a series of plates of different form and shape, in which the current flows in a zigzag manner. In lieu of using the additional tongues, as in the previous figures, I attach small lengths of coiled wire. The coils give a springy character to the belt or article to which they are attached, without disconnecting one plate from the next, and also without interfering with the electrical action of the elements.

Figure 5:
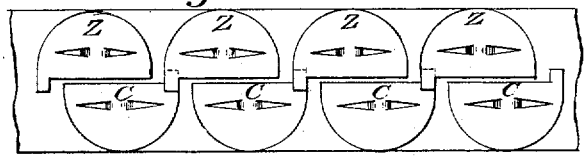

Fig. 5 is a modification of the shape of the plates shown in Fig. 3, the difference being that these plates are made with a tongue at the corner of each of them, and these lie upon one another or overlap in voltaic order in elements or single batteries; but they may be connected to form a continuous band or pad by either of the above-mentioned methods, or in any other way found suitable.

Figure 6:
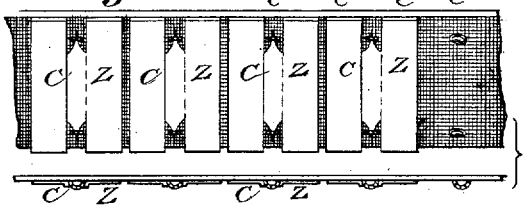

Fig. 6 shows a series of plates, C Z, with the tongues also formed at the edges, but with the points not projecting beyond the edges. In this case the points are passed under loops formed either in the weaving of the fabric or by means of a sewing-machine after the fabric is made. These plates are cut from long strips of metal, two edges of which—say one of copper and one of zinc—are overlaid throughout their whole lengths, and soldered together before the plates are stamped out or otherwise produced, the tongues or lips being made at the part where the plates are overlapped.

In the foregoing I have shown a few forms of plates and the modes of attaching them to the fabric or backing; but there are other ways of doing this, such as with separate pins or tongues, which can be passed through holes in the plates as well as through the fabric.

In speaking of the fabric I do not strictly mean by fabrics those which are woven, as a felted or a netted body is equally applicable, and this may be coated or impregnated with a solution of any acidulated liquid, to assist the exciting action of the perspiration thrown off from the body.

The parts of the fabric which are not covered by the plates may be coated with an adhesive substance, such as those before referred to, and which will adhere to the flesh of the human body with tenacity, without interfering with the movements; or the plates themselves may be more or less coated with such substance, to enlarge or reduce the surfaces which are intended for the electrical or galvanic action on the part affected.

Figure 7:
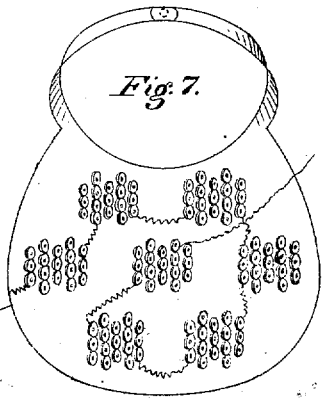

In Fig. 7 I represent an article known as a "chest-protector." I propose to cover one face of this by metal beads or tinsels, which can be sewed on or otherwise attached, the beads being arranged in clusters, connected in a similar voltaic manner as the plates before mentioned.

Figure 8:
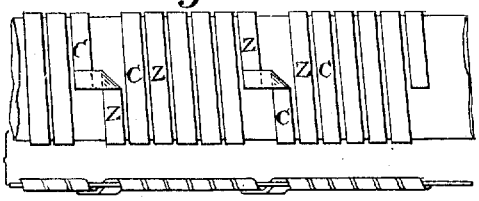
Figure 9:
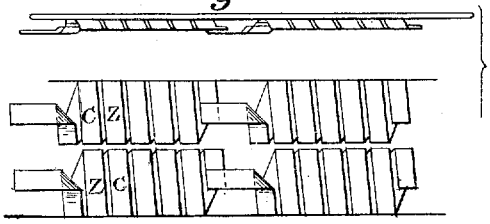

Fig. 8 represents a portion of a band or belt, in which the galvanic plates (positive and negative) are formed of long narrow plates or strips, C Z, bent into spirals, the metals forming one element being soldered, as before explained. In this arrangement the fabric (absorbent or not) is lodged in the coils, and acts as a band for retaining the plates in place. This band or lining may be composed of or be connected with a porous material, to permit of the air passing through it. According to this figure the spirals are placed end to end; but one coil could be below the other, as shown in Fig. 9. This figure shows the spirals attached to the backing, to which the absorbent can be attached; or an absorbent could be passed into the folds of the spiral and secured in any suitable manner. The backing or the lining may, in some cases, be formed with recesses or channels for holding the absorbent material, such as a fibrous pulp or sponge, and this pulp or the sponge may be mixed or impregnated with a salt or a chemical compound possessing exciting and depolarizing properties; or the plates themselves may be bent or shaped into the form shown in Fig. 10, so that the absorbent can be prevented falling out or escaping should too much liquid be supplied by accident or otherwise. In this view I have shown all the copper plates C at the front or wearable side, and the zinc plates at the back, and these are prevented from touching the copper plates, except the proper places, by a fabric or sheet which acts as an insulator.

Figure 10:
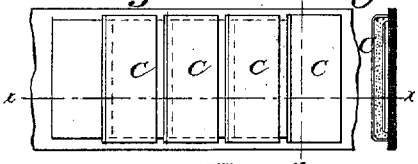
Figure 12:
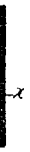
Figure 11:
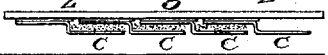

Fig. 11 is a transverse sectional view on the line *x x* of the series of the plates shown in Fig. 10, and Fig. 12 is a vertical section through the line *z z*. I have not indicated how these elements should be secured to the fabric; but they may be sewed, pinned, or otherwise fastened thereto, so that a faulty plate or a faulty element could be easily renewed should occasion require it.

The object of the second part of my invention is to make magnetic bands, belts, and articles to be worn or applied to the body in a similar manner and by similar means to those referred to in the first part, whereby a gentle self-sustaining magnetic action is kept up on the affected parts or throughout the whole body. I sew or otherwise secure thin plates, strips, or other pieces, bent or not, of magnetized steel, hardened, tempered, or annealed, in or to a fabric or web, in sections, each section being composed of four, five, or more pieces, in direct contact, to form compound magnetic staves, horseshoes, or elements, and these may be connected to other similar elements in any convenient manner, so as not to interfere with the movements of the wearer.

Figure 13:
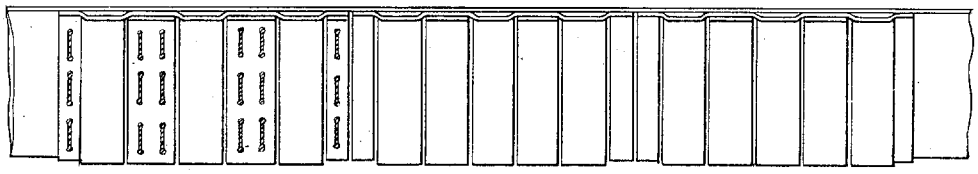
Figure 14:
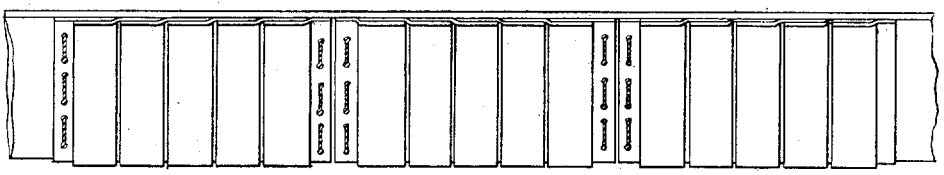
Figure 15:
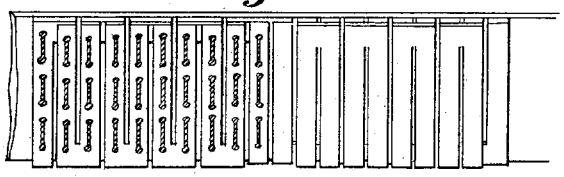

Figs. 13, 14, and 15 show separate forms or shapes of steel plates sewed on or to a backing. In Fig. 13 the plates are flat and bent plates arranged alternately. The flat plates are pierced with holes, which correspond with other holes pierced in the flanges of the bent plates, so that one sewing serves to fasten both of them in place. In Fig. 14 each plate is bent, and the sewing is through the holes of the flanges, which are covered by the overlap of the neighboring plate. Thus a smoother surface is produced than in the previous figure. In Fig. 15 the plates are all flat and cut like the letter U, but with the corners square, so that the whole of the surface is in contact. These, like the other plates, may be pinned, riveted, or eyeleted on or to the backing in lieu of being sewed on.

I have only given these three examples of what I desire to claim in this part of my invention. I may, however, state that the plates may be wound into spiral or any other shape before they are fastened on the backing.

The object of the third part of my invention is to make self-sustaining bands, belts, and other articles, of a combination of elements such as those described in the first and second parts, before referred to, in order to produce combined electrical, galvanic, and magnetic action.

I have not shown in any figure how I attach a copper or zinc plate at one part of the articles and a steel plate at another, for the purpose referred to, because that will be readily understood, and also because the plates would be of similar shapes to those already given or described.

The next part of my invention relates to chains, bands, pads, garments, or articles of dress which are to be secured on or to the body by tapes, cords, straps, or other fastenings, and which are to be supplied with an exciting liquid, for the purpose of establishing a continuous electrical or galvanic action throughout the same, for treating diseases and complaints, as above referred to. I have, in the following figures, shown several examples of these.

Figs. 16 and 17 are front and back views of a band in which the elements are formed of narrow, thin lengths of copper and zinc, one of which is insulated from the other by a cord or thread wound in distance spirally upon it before the strips themselves are laid in position to be wound into plates or elements. The edge cords maintain the elements at their respective distance apart, and the voltaic arrangement is obtained by securing the ends of the one metal strip to the opposite metal strip of the next element by soldering. By this means a perfectly flexible band is produced, which can be bent to set upon any part of the body, or be wound upon the leg or arm, as desired. In some cases I fit a strip of absorbent material the full length of the band, inside the elements, so that when dipped into exciting liquid the whole of the elements become moistened. In others I make a bulge or raised part at the back of the band to hold a perforated tube, through which a liquid can be forced for the purpose of charging the absorbent. This will be understood by referring to Fig. 18, where the channel is formed in the center.

Figure 19:
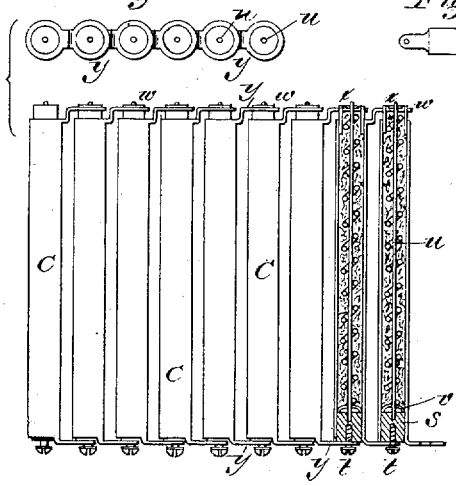

Fig. 19 represents a number of elements of a plain character, in which the chemical body or compound inserted can be retained by stoppers *s*, which may be tapped for a threaded pin, *t*, to be screwed down upon a central wire, *u*, to push it through the other end sufficiently to give a finger-hold to withdraw it by. In this withdrawal the cup-leather *v* cleans the copper completely out, and takes the zinc, which is wound spirally round it, at the same time.

When the fresh quantity of chemical agent and zinc is put in, the screw-pin *t* is turned partially back, and the central wire *u* caused to bear upon it, to form a conducting medium from the zinc to that end of the next element. The other end of the copper plate has a metal tube, *w*, insulated from the copper, pushed into it, and this is in contact with the zinc in the inside of the cylinder. There is a washer or disk, *x*, for retaining the depolarizing compound in place. The eye or perforated piece *y* of the cylinder passes over the insulated tube *w*.

Figure 21:
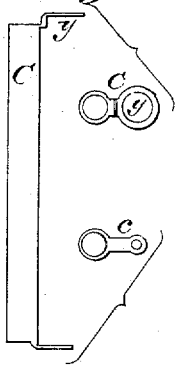
Figure 20:
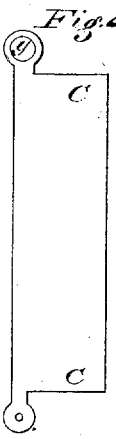

It will be seen by the detached view, Fig. 20, that the lips in which the eyes are made are stamped out with the plate, and are bent in a proper manner after the tubular part is shaped, the eyes being of different sizes, as in Fig. 21—one to suit the tube *w*, and the other the screw-pin *t*, the head of which limits the movements of the lips and prevents false contacts. The lip at the screw-pin end is prevented touching its neighboring copper plate by the projecting portion of the stopper *s*.

Figure 22:
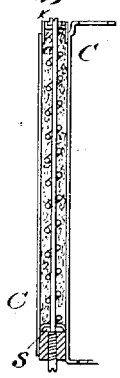

It is not essential that the screw-pin should have a head, as, when it and the central wire are made from one piece of metal, a nick can be made at each end, as shown in Fig. 22.

Sometimes two zinc wires can be used in each copper tubular plate, in the manner represented in Fig. 23, and then they are provided with a cupped leather at each end, as more clearly seen in Fig. 24. The outer leathers of each wire are here covered by a non-conducting disk, *z*, to prevent the lip of the adjoining copper plate making false contacts, the disk *z* being rather larger in diameter than the copper plates for the purpose. In these last two figures the lips are bent round to form eyes or loops, in lieu of being perforated, as previously spoken of.

I propose to fit a coiled piece of springy insulated metal between the two inner leathers to force them apart, and thus keep the outer ends of the central wires outside the disks *z*, for connecting purposes; and when the salt or chemical core requires renewing, it can be done by simply pushing the central wires in to detach it from the lip, which can then be moved to one side, to enable the faulty core to be withdrawn and a fresh one inserted, when, by overcoming the tension of the spring, the connection can be remade.

Figure 25:
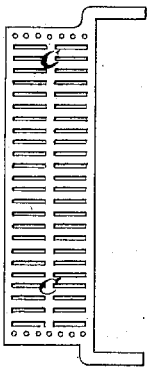
Figure 26:
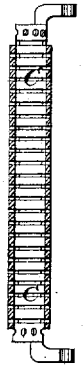

Plates made with the last form of lips can be perforated or slotted, as seen in Figs. 25 and 26, as well as those with the previous ones.

Figs. 27 and 28 represent the copper plates stamped into trough form, so that the zinc plate can be inserted and held therein by a wire, which is passed through insulated holes at the ends of the troughs, the wires projecting to engage with the lips of the next copper plate of the adjoining element. I prefer to pinch the zinc plates in close contact with the central wires, so as to retain them in position, and to prevent false electrical contacts occurring.

The copper troughs may be of any dimensions, and can be pressed to any depth, so that a band, chain, or other battery can be constructed of great intensity of action in a comparatively small size, and these, if held in a frame in a rigid manner, will be found suitable for sending currents along wires, if attached to an ordinary telegraphic sending-instrument.

Figure 31:
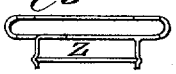
Figure 29:
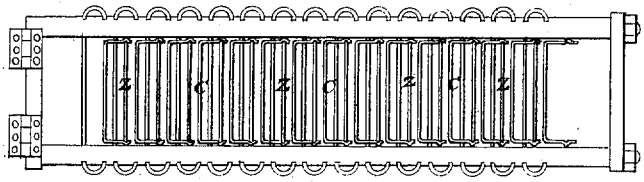
Figure 30:
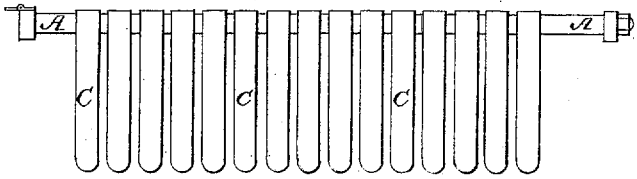

In the trough-battery shown in Figs. 29 and 30, I propose only to bend the lips outward, and to form two of them from one side, so that they may both touch the zinc plate of the adjoining elements, the lips being slightly recessed, as shown in the detached view, Fig. 31, to hold the zinc plate firmly. The other sides of the troughs have their lips entirely removed, and the slots or notches are somewhat larger than the slots or notches on the lip sides, for the purpose of permitting the lips of the next copper plates to pass in without touching.

Figure 32:
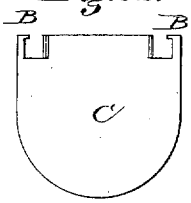
Figure 33:
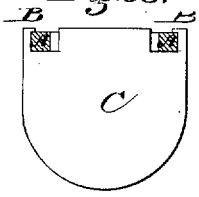

I maintain the rigidity of the battery by bars of ebonite or other hard non-conducting substance, A, which are forced into the slots; and these are prevented falling out, or even shifting their position accidentally, by the points B B taking over them as shown in the side views, Figs. 32 and 33.

Another form of bending or stamping the copper plates into is the box shape—that is, with four raised sides or edges—into which the zinc plates can be fitted, and access of exciting liquid is obtained through the crevices or perforations either at the bottom, at the sides, or at the top; or, if the depolarizing-salts or chemical compound be used, the lids can be opened, when both sides of the zinc plate can be got at.

Figure 34:
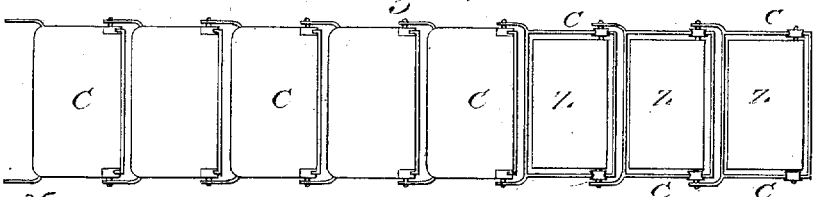
Figure 35:
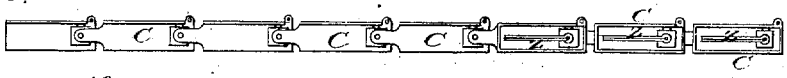
Figure 36:
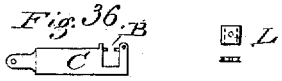

In Figs. 34 and 35 I have shown a few elements in voltaic arrangement, through lips which are perforated to receive the wires in a similar manner to those described, these wires being insulated from the copper of its own element by small buttons or filling-in pieces of ebonite, L, which are forced into the apertures in the side walls of the box, and then retained by the projections B in Fig. 36, which are pressed down upon them, and thus a chain in regular voltaic contact is formed.

The zinc, when placed in the box, may rest upon a layer of depolarizing-salt or chemical compound, and another layer can be laid above it; or it may be inclosed in paper or fibrous material of an absorbent character, for the purpose of retaining the moisture, to insure the continuous electrical action.

The zinc plates are, preferably, doubled or folded over, and the wires are pinched in the folds, so that they form the hinge-pins upon which they can be turned up to renew the salt, and are also the hinge-pins upon which one side or lid of the copper box moves.

There are many ways of fastening the end plates or pieces of metal upon the end elements of voltaic bands or chains, for the purpose of applying the current to any particular part of the person that may require to be acted upon; and in order that the intensity or power of the current can be brought to bear upon a larger or a smaller surface of the body at will, I have invented a fastener by which these objects can be obtained. The fastener is shown in detail in Figs. 37, 38, 39, and 40 of the accompanying drawing.

Fig. 37 is an inside and a sectional view of the disk K of one pole of the battery. The inner face has a disk of copper soldered on it, and this holds a T-headed pin of non-conducting metal in its center, so that it can be turned by the fingers. The pin is passed through the spiral coils or the plates before spoken of, and through a slot in the back plate shown in Fig. 38, after which it is turned a quarter round to hold the disk securely. The pole at the other end of the band or chain is formed in a similar manner, and its T-headed pin is passed through the spiral coils or the plates, and also through the back plate, before the pin is turned a quarter round to secure it. The inside disk in this pole terminates in a tongue, which projects beyond the edge, and is perforated, so that a hook can be attached to combine other elastic bands therewith, as will be understood by referring to Figs. 39 and 40. The poles are prevented turning on the pins when in position by the edges of the plates being turned down to hold them firm.

The electrical action of the disk K (shown in Fig. 37) can be enlarged or diminished at will by drawing a canvas cap over the edges, more or less, by a cord laced into the edges.

Having thus described my invention, what I claim is—

1. The construction and combination of plates or other pieces of metal for forming chains, bands, garments, or other articles, as herein described, for application to the human body, as and for the purpose set forth.

2. The fasteners for said belts, chains, bands, &c., constructed to operate as set forth.

3. The trough-shaped batteries, constructed substantially as shown and described.

4. The metal plates having the lips formed thereon, for securing them to the fabric in the construction of belts, chains, &c., substantially as set forth.

5. The flat metal strips, bent in spiral form, and arranged upon a fabric, in the manner and for the purpose described.

6. The employment of steel plates, arranged in groups or elements on a fabric, for the purpose of applying portable magnetism to the body, as set forth.

7. The bands composed of spirally-wound wire, in which channels are formed for holding and retaining absorbent material, substantially as described.

8. A chain or band composed of a series of tubes, constructed and combined substantially as shown in Figs. 23 and 24.

9. A galvano-electric band, chain, or garment, provided with an adhesive coating for securing or attaching it to the body, substantially as described.

ISAAC LOUIS PULVERMACHER.

Witnesses:
E. N. DANIEL,
166 *Fleet Street, London.*
J. S. ROBINS,
2 *Waterloo Place, Pall Mall, London.*